(12) United States Patent
Kanareykin et al.

(10) Patent No.: US 8,922,208 B1
(45) Date of Patent: Dec. 30, 2014

(54) OPTICALLY PUMPED MAGNETICALLY CONTROLLED PARAMAGNETIC DEVICES FOR MICROWAVE ELECTRONICS AND PARTICLE ACCELERATOR APPLICATIONS

(75) Inventors: Alexei Kanareykin, Rockville, MD (US); Paul Schoessow, Lakewood, CO (US); Sergey Antipov, Darien, IL (US); Oleg Poluektov, Clarendon Hills, IL (US)

(73) Assignee: Euclid Techlabs LLC, Solon, OH (US)

( * ) Notice: Subject to any disclaimer, the term of this patent is extended or adjusted under 35 U.S.C. 154(b) by 714 days.

(21) Appl. No.: 12/761,665

(22) Filed: Apr. 16, 2010

Related U.S. Application Data

(60) Provisional application No. 61/169,904, filed on Apr. 16, 2009.

(51) Int. Cl.
 *G01R 33/00* (2006.01)
 *G01R 33/02* (2006.01)

(52) U.S. Cl.
 CPC .................................... *G01R 33/02* (2013.01)
 USPC ........................................................ 324/260

(58) Field of Classification Search
 None
 See application file for complete search history.

(56) References Cited

U.S. PATENT DOCUMENTS

| | | | | |
|---|---|---|---|---|
| 3,710,163 | A | * | 1/1973 | Bomko et al. ............. 313/360.1 |
| 5,287,381 | A | * | 2/1994 | Hyuga et al. .................... 372/75 |
| 6,828,789 | B2 | * | 12/2004 | Hyde et al. ..................... 324/316 |
| 7,858,307 | B2 | * | 12/2010 | Ho ................................ 435/6.11 |
| 2004/0245085 | A1 | * | 12/2004 | Srinivasan .............. 204/157.15 |
| 2007/0048870 | A1 | * | 3/2007 | Xiang et al. .................... 436/56 |
| 2008/0070195 | A1 | * | 3/2008 | DiVito et al. ................. 433/224 |

FOREIGN PATENT DOCUMENTS

SU 859978 A * 10/1984

* cited by examiner

*Primary Examiner* — Paresh Patel
(74) *Attorney, Agent, or Firm* — John D Gugliotta

(57) ABSTRACT

An active device is provided that is energized by an optical source and uses an active paramagnetic medium to transfer this energy to a resonant circuit enabling new classes of electronic components.

24 Claims, 5 Drawing Sheets

OPTICALLY PUMPED MAGNETICALLY CONTROLLED PARAMAGNETIC DEVICES FOR MICROWAVE ELECTRONICS AND PARTICLE ACCELERATOR APPLICATIONS

RELATED APPLICATIONS

The present application claims benefit of U.S. Provisional Application 61/169,904 filed on Apr. 16, 2009 and incorporated by reference herein as if fully rewritten.

BACKGROUND OF THE INVENTION

1. Technical Field of the Invention

The present invention is in the technical field of microwave electronics, in particular to microwave components (amplifiers and attenuators) in which an active paramagnetic material is energized by an optical source and transfers this energy to a resonant microwave circuit or resonant cavity. The characteristics of this device are controllable by an external magnetic field. A particular application of this technology is to power a compact linear particle accelerator that is energized by an optical source and utilizes an active paramagnetic medium to transfer this energy to a charged particle beam.

2. Description of the Background Art

Conventional microwave amplifiers use solid state or vacuum tube technology to add energy to a low level signal while maintaining the same frequency and phase characteristics of the input signal. In these technologies electrical energy supplied to the circuit provides the energy to amplify the signal. Furthermore, control of the gain and frequency characteristics of the device if present also make use of electrical signals. While it is possible to add components and circuitry to provide external control (via a magnetic field) or to energize the amplifier using and optical source of energy, these options are not intrinsically part of the amplifier.

Conventional linear particle accelerators use a high frequency microwave or radio frequency (RF) generator for energizing a resonant cavity to transfer energy to a charged particle beam. The resonant cavity is commonly comprised of a metallic shell fitted with a series of copper disks inside the shell. In addition, a vacuum channel is provided through the center of the disks to transmit charged particles along the central symmetry axis. An alternative technique substitutes a dielectric tube in place of the disks.

In such embodiments, the use of existing materials with sufficiently large high field breakdown strength form limitations on the cost, size and weight. Similarly, the mechanisms for generating the energy necessary to accelerate the particles as rapidly as possible also lead to large cost, weight, and space requirements. This is particularly problematic for the use of accelerators as research instruments for universities or for applications at small or remote medical facilities.

Further, the size requirements of present technology accelerators preclude any portable applications, for example, for explosive or contraband material detection.

Further still, the lack of phase balance or other controls of the charged particle beam and the accelerating wave in such accelerators lowers the acceleration efficiency.

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

The present invention is an electronic technology that uses a paramagnetic material energized by an optical pump signal to transfer microwave energy to a circuit or a particle beam.

SUMMARY OF THE INVENTION

1. Technical Problem

The present invention is a new type of solid state technology that uses a paramagnetic material energized by an optical pump signal to amplify, attenuate, or otherwise modify a microwave signal using a magnetic control field. The optical pump energy can be provided by a laser diode or by solar energy. The magnetic control signal can also be used as a sensitive magnetic field probe. The present invention is also useful as a particle acceleration technique that uses a paramagnetic material energized by an optical pump signal to accelerate a particle beam to high energies.

2. Solution to Problem

Briefly described according to a broad embodiment of the present invention, a technology for the basis of new microwave circuit components is provided that is energized by an optical source and uses an active paramagnetic medium to transfer this energy via an inductor to an external circuit.

Briefly described according to another broad embodiment of the present invention, a microwave amplification technique is provided that is energized by an optical source and uses an active paramagnetic medium to transfer this energy to a circuit or charged particle beam.

3. Advantageous Effects of Invention

In accordance with a preferred embodiment, the aim of said invention is to enable the amplification or modification of an input microwave signal using a magnetic control signal and optical pumping. The unique properties of the paramagnetic medium on which the invention is based will allow the development of circuit components that can be used to couple energy into or out of a resonant circuit or cavity.

The advantages of the present invention include, without limitation, that it is versatile, compact and can form the basis for a number of electronic and accelerator devices. The basic technology forms the basis for the following classes of circuits:
  a. low noise solar or laser driven microwave amplifiers;
  b. microwave amplifiers or attenuators with properties adjustable using an external magnetic field;
  c. multi-pole active analog filter networks using inductors with active paramagnetic cores;
  d. active metamaterials with refractive properties controllable using optical and magnetic means;
  e. highly sensitive magnetic field sensors; and
  f. compact optically driven linear accelerators for medical or security screening use.

The use of feedback from the circuit to the magnetic control signal of the active core inductor offers the possibility of realizing nonlinear device properties not presently available. In accordance with a preferred embodiment, the aim of said invention is to enable the circuits and devices described in points a-f above.

The advantages of the present invention include, without limitation, that it is compact and does not require a complex infrastructure to operate. The use of visible light as the power source permits sensors and rf components based on the device to operate autonomously in spacecraft and remote locations.

It will be possible to set up and operate a particle accelerator based on this device at hospitals in underdeveloped countries to be used for isotope preparation, cancer therapy and imaging. Small research institutions will also be able to purchase and operate such an accelerator in cases where the cost of a conventional linear accelerator is prohibitive.

Further, a device incorporating the present teachings would be sufficiently portable to use for cargo and baggage screening for security purposes.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 1:
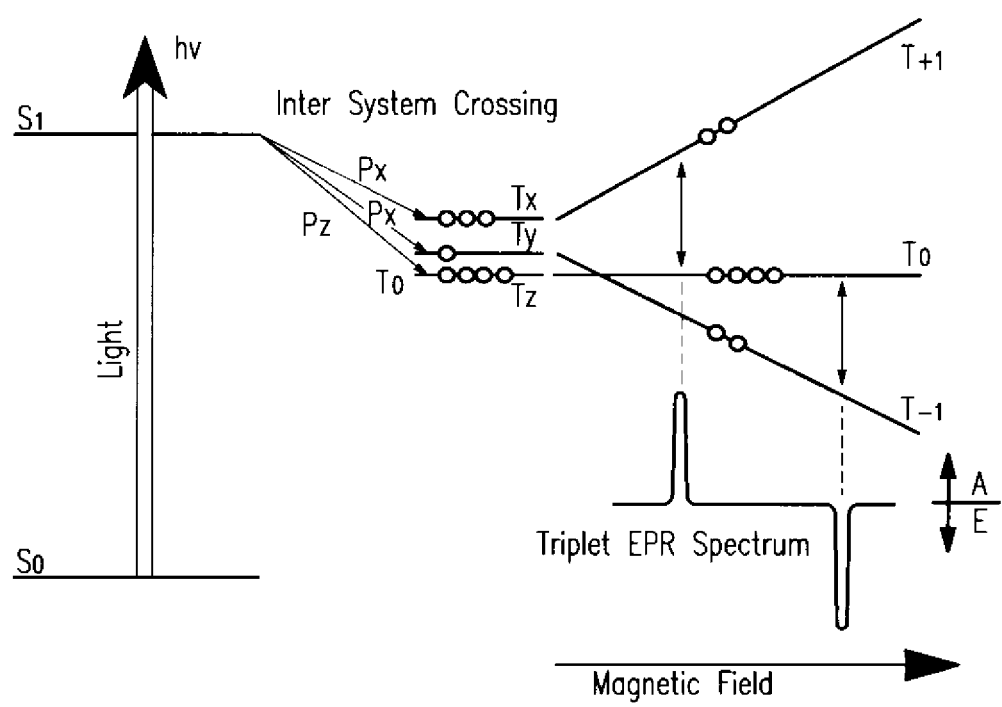
FIG. 1 is a simplified energy level diagram of an optically pumped active paramagnetic medium.

An active material is one in which a population inversion exists and thus can undergo stimulated emission of electromagnetic radiation. Equivalently, an active material has a negative imaginary part of its permittivity or permeability. In a paramagnetic active medium such as PCBM the imaginary part of the magnetic susceptibility $\chi''$ is negative in some range of frequencies, i.e. the medium stores energy and can transfer this stored energy to an electronic circuit or charged particle beam. The possibility of a microwave device based on this technology was previously theoretically suggested by the existence of a large class of X-band and higher frequency paramagnetic active materials as observed via time resolved electron paramagnetic resonance (EPR) spectroscopy. These materials were found to retain activity at relatively high temperatures and possess reasonably high energy densities when pumped by an optical source such as a laser or flashlamp.

For particle accelerator applications, advantages to working in the microwave are the less stringent mechanical and electron beam quality requirements compared to IR or visible wavelengths, and the ready availability of diagnostics and test equipment.

In order to accomplish the teachings and benefits of the present disclosure, an active paramagnetic medium must first be developed to transfer optical energy to a circuit or charged particle beam. An active microwave medium is preferably developed from a complex organic system ($C_{60}$, $C_{60}$—R, Tetraphenyl Porphyrin (TPhP)) in an organic solvent, although solid state media like ruby may also be used. Focusing principally on the use of an optical or infrared wavelength active medium to provide the energy for accelerating electrons, studies of electron paramagnetic resonance (EPR) in solutions of fullerene or porphyrin compounds have demonstrated activity (negative imaginary part of the magnetic susceptibility) in the ~10 GHz frequency range when the material is optically pumped. Unlike conventional solid state maser materials, the C60 based materials can operate at relatively high temperatures. Based upon these materials new active paramagnetic materials have been developed and synthesized with improved gain and bandwidth properties. Development of suitable active materials has herein overcome a number of challenges in proceeding from EPR spectroscopic samples to bulk quantities of material required for PASER acceleration tests. After testing a large number of candidate materials and identifying the best ones in terms of $\chi''(\omega)$ ($=\text{Im}(\mu(\omega))/4\pi$) and bandwidth, the materials are therein prepared in a form that can be easily placed in a cylindrical waveguide. In one preferred embodiment, the active component is dissolved in a solution of polystyrene and toluene. The toluene is then evaporated under vacuum leaving the active material in a solid matrix.

In order to evaluate the usefulness of the active media for particle acceleration, a test system was provided to measure the electromagnetic properties of active media loaded prototype accelerating structures using standard microwave techniques. As shown in conjunction with FIG. 1, the material is immersed in a direct current (DC) magnetic field $B_0$. Free radicals (molecules with unpaired electrons) are created by excitation with a light pulse (photolysis) or electron beam (radiolysis). The basic EPR resonance condition in a paramagnetic spin system is $\hbar\omega_0 = g\beta H_0$, where $\omega_0$ is the resonance frequency, $\beta$ is the Bohr magneton, and H is the magnetic field strength. The g-factor varies for the most part between 1 and ~2 depending on spin-orbit interactions in the material; many radicals and paramagnetic complexes have g-factors larger than 2.

FIG. 1 shows a very schematic diagram of the energy levels in these systems relating to pumping of the medium. An optical photon excites an electron from the ground ($S_0$) state of the molecule to the $S_1$ state. Through a nonradiative process referred to herein as intersystem crossing, electrons can undergo transitions from the $S_1$ state to the lower energy triplet state $T_0$. Depending on the magnetic field strength the levels of $T_0$ are split and can even cross over as in the case of the levels marked $\tau_0$ and $\tau_1$. These states possess a nonequilibrium population of electrons, i.e. a population inversion. A system with sufficiently high magnetic fields will exhibit both emission and absorption lines. As a result the magnetic susceptibility in our measurements shows both emission and absorption peaks.

Developed active materials were evaluated using time resolved EPR spectroscopy. Standard measurement techniques and commercial equipment were used for characterization of these materials.

Figure 2B:
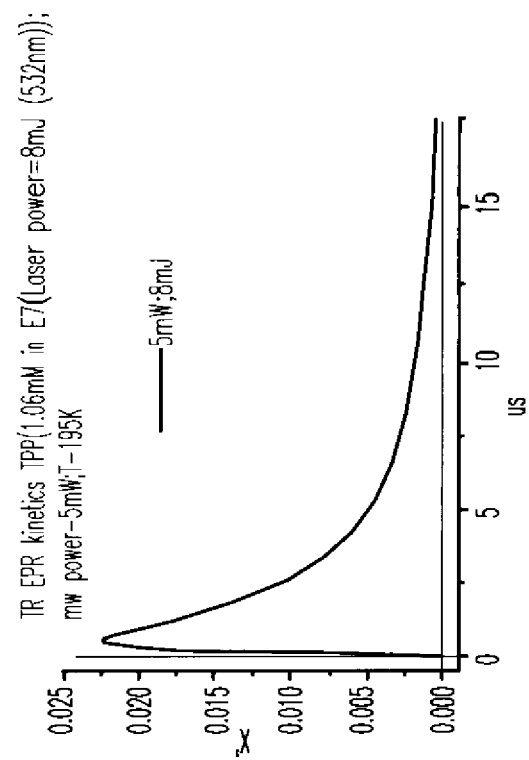
FIG. 2b is a time resolved EPR signal from TPhP-negative regions of the wave correspond to frequencies at which acceleration can occur.
Figure 2A:
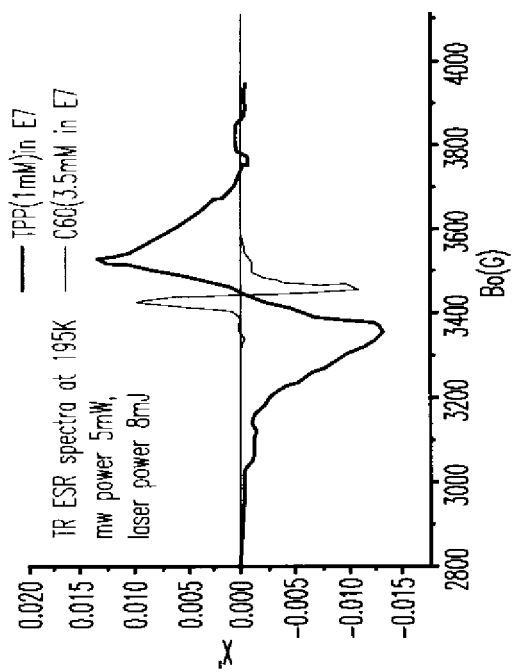
FIG. 2a shows Electron Paramagnetic Resonance (EPR) spectra showing population inversion in $C_{60}$ and TPhP.

FIG. 2a-2b show EPR spectra of materials exhibiting a high susceptibility. The EPR data obtained as a function of the applied magnetic field for a constant rf frequency (9 GHz) over a small time interval is shown in FIG. 2a. FIG. 2b is a plot of the time dependence of the maximum EPR signal at a constant H field (corresponding to the position of a resonance peak) as a function of time. The decay time constant of the signal is ~3 µs, large compared to the time required for a relativistic beam to traverse an accelerating structure. Dependence of the susceptibility on the optical pump intensity for these mixtures is close to linear; deviations from linearity result from saturation of the inversion population.

Figure 3A:
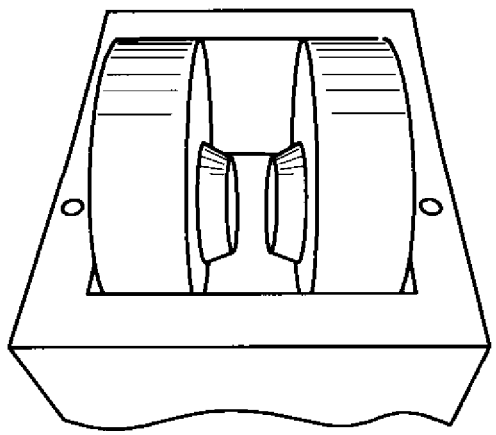
FIG. 3a is a schematic drawing illustrating the basic active resonator idea.

A schematic diagram of the basic application for this material is shown in FIG. 3a. A sample of the active material is immersed in a DC magnetic field corresponding approximately to the EPR resonance of the material. In actual practice this field would be provided by a rare earth permanent magnet to obtain the smallest form factor although an electromagnet could be used for non space critical applications. The active material is located inside an inductor that forms part of a resonant LC circuit. A second coil is used to fine tune the DC magnetic field applied to the paramagnetic material, allowing for adjustment of the permeability and hence the gain, bandwidth, and resonant frequency of the circuit.

As would be apparent to one skilled in the relevant art such a configuration represents merely a design choice, and it would be understood, in light of the present teachings, that other configurations of the circuit would provide similar or equivalent results, including, but not limited to, a configuration having a cylindrical cavity loaded with the active medium acting as the resonant circuit, or with an axial vacuum channel for the beam passing through a solenoidal magnetic field.

Figure 3B:
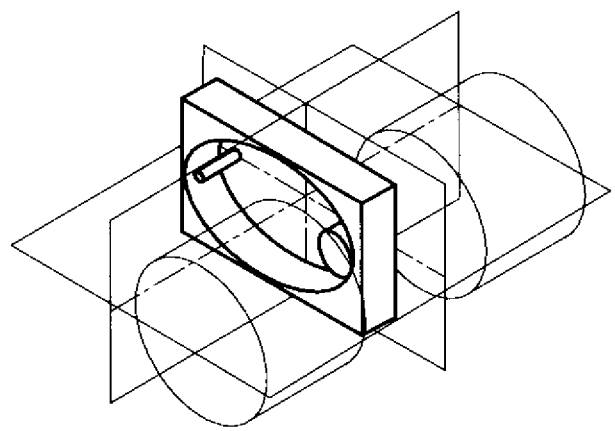
FIG. 3b is a conceptual drawing of the device in FIG. 3a in a circuit board mountable configuration.

Referring to FIG. 3b. A conceptual design of the active device for use as an element on a circuit board. In such a configuration a thin slab of the plasticized active material is bonded to a thin permanent magnet positioned on the board and surrounded by a coil to form an active inductor.

Figure 4:
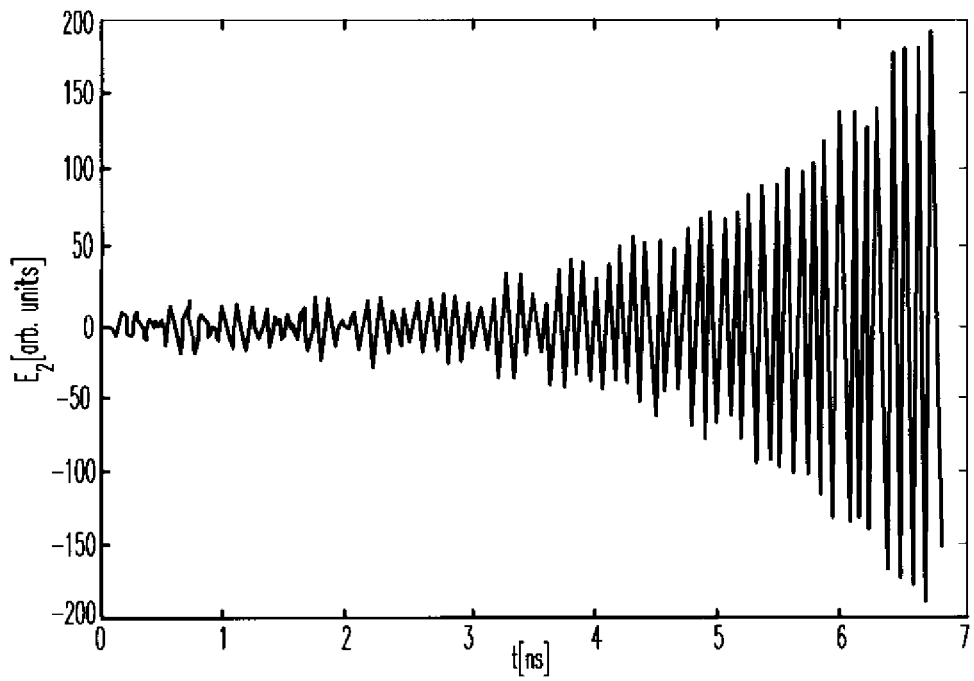
FIG. 4 depicts an Arrakis simulation of the time evolution of the signal on an axial electric field probe at the center of the test cell.

The active medium parameters are approximately those of the TPhP measurements shown in FIG. 2: $\chi''_{max}=0.022$, FWHM≈200 MHz. The effective medium approximation for frequency dependent permeability has been incorporated into the Arrakis code. FIG. 4 depicts an Arrakis simulation of the time evolution of the signal on an axial electric field probe at the center of the test cell. The time evolution of the axial electric wakefield at the cavity center is shown. The amplification of the fundamental mode is apparent, and the sampling time (~7 ns) required to observe a voltage gain of approximately a factor of 10 is still short compared to the lifetime of the excitation (~3 µs).

Figure 5:
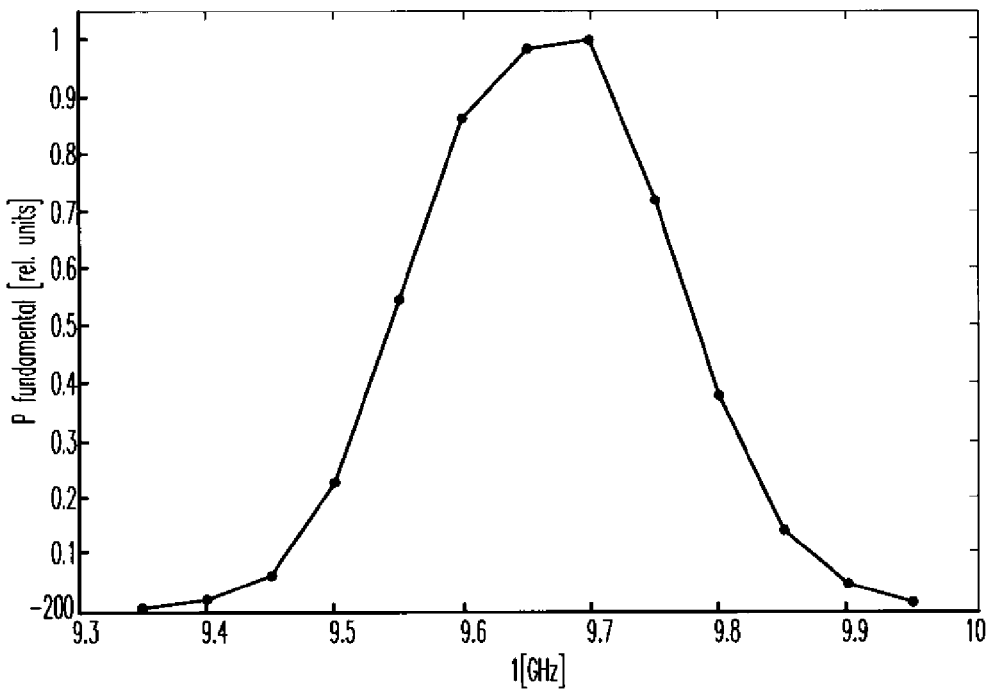
FIG. 5 depicts an Arrakis simulation of the cavity power in the fundamental mode at ~7 ns as detected by field probe of FIG. 4 as a function of the resonant frequency of the medium.

FIG. 5 is a plot of the signal power as a function of the resonant frequency $f_0$ of the medium. Since the resonant frequency is also proportional to the DC magnetic field ($df/dH=2.8$ MHz/Oe), FIG. 5 is equivalent to doing a field scan with the EPR magnet to search for the optimum signal and determine the resonant frequency of the medium.

Figure 6:
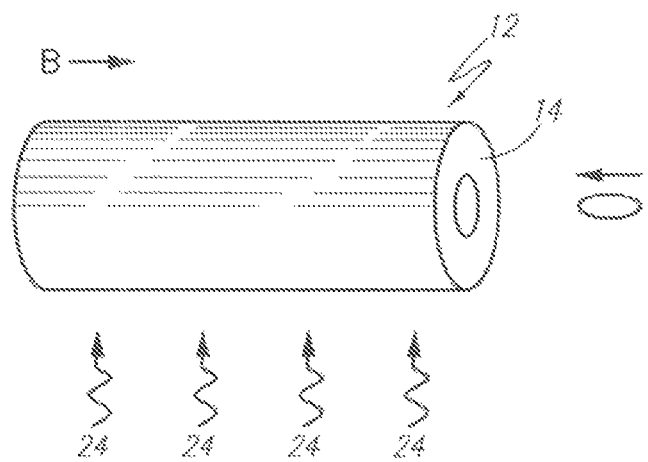
FIG. 6 is a sketch of the optically driven particle accelerator concept according to an exemplary embodiment of the present invention.
Figure 7:
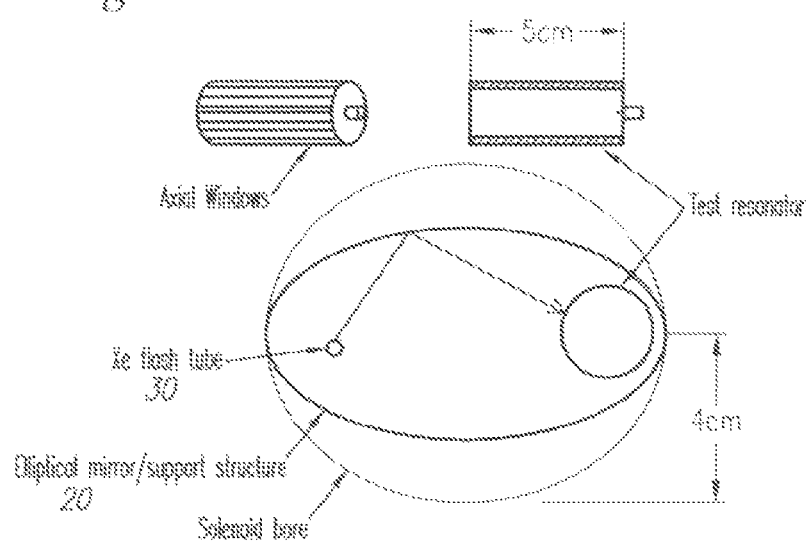
FIG. 7 is a sketch showing the principle of an optically driven particle accelerator using an elliptical mirrored optical pumping system.
Figure 8:
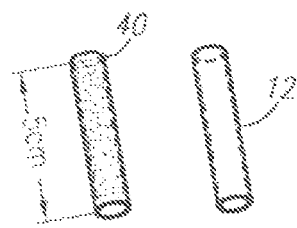
FIG. 8 is a photograph of the active medium used in the optically driven particle accelerator in a solid (polystyrene) matrix.

In accordance with a preferred embodiment of the present invention, as shown in FIG. 6-8, an optically driven particle accelerator concept is shown, generally noted as 10, according to a basic depiction of the present invention. A cylindrical tube 12 forms the accelerating structure and containing a liquid active paramagnetic microwave medium 14. For purposes of the present invention it is felt the medium 14 can alternately be fabricated from a plasticized solid microwave active medium to form the accelerating structure.

In either embodiment the medium 14 is held in a constant magnetic field provided by a solenoid. The entire accelerator is positioned inside the bore of the solenoid 24. It is anticipated that the energy of the microwaves is generated through the excitation of the medium 14 by a visible light pulse from a xenon flashlamp 30, laser or other optical source. The light pulse is concentrated on the accelerating structure using an elliptical mirror 20. The effect of the optical excitation is to create a population inversion between two Zeeman levels in the active medium 14. The excited medium 14 can then transfer its energy to a charged particle beam 40 passing through the cylinder 12. This energy transfer is by the particle acceleration by stimulated emission of radiation (PASER) effect. The charged particle beam current spectrum needs to have substantial frequency content corresponding to the energy difference between inverted levels. This can be accomplished in a number of ways: through the use of a short pulsed beam; a dc beam modulated at the frequency difference of the inverted levels; acceleration at the leading edge of a dc beam; or use of a sufficiently low intensity beam that the fields of the individual charged particles rather than the collective field of the beam trigger the PASER effect.

For the purposes of the present invention, it is anticipated that the accelerating tube may be either resonant or nonresonant, with the configuration differing only with respect to the size and surface conditions (conducting or open boundaries) of the structure.

In conjunction with reference to FIG. 7, the construction details of the present invention are shown. The accelerating structure is located inside an elliptical mirrored cavity 50 with its center at one focus of the ellipse. The mirrored cavity 50 serves to focus the light from the flashlamp 52 onto the active medium accelerating structure. The mirrored cavity 50 may be made of any nonferromagnetic material, and the interior is polished and aluminized to obtain a mirror finish. At the other focus of the ellipse is located a linear xenon flash tube. The mirrored cavity is located inside the bore of a solenoid magnet. The solenoid provides the necessary constant magnetic field for the activity of the paramagnetic material. The accelerating structure 54 is located at the other focus of the mirror. The endcaps for containing the active medium are not shown for clarity.

Referring now to FIG. 8, a test sample of the plasticized active paramagnetic medium is shown. To form this active material, the fullerene derivative compound [6,6]-phenyl-$C_{61}$-butyric acid methyl ester (PCBM) is dissolved in the solvent toluene at a concentration of 1 mmol. Powdered polystyrene is dissolved in the toluene-PCBM solution until a thick slurry is formed. The toluene-polystyrene-PCBM solution is poured into a mold of desired shape. The toluene is then evaporated under vacuum to produce an optically transparent plastic loaded with the active PCBM compound.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

Having thus described the invention what is claimed as new and desired to be secured by Letters Patent is as follows:

1. An apparatus for transferring energy to a microwave circuit or charged particle beam comprising:
   an active microwave chamber that is energized by an optical source and utilizes an active paramagnetic medium to transfer energy from the active medium to the microwave circuit or charged particle beam, wherein said paramagnetic medium comprises fullerene derivative [6,6]-phenyl-$C_{61}$-butyric acid methyl ester (PCBM).

2. An apparatus for transferring energy to a microwave circuit or charged particle beam comprising:
   an active microwave chamber that is energized by an optical source and utilizes an active paramagnetic medium to transfer energy from the active medium to the microwave circuit or charged particle beam, wherein said paramagnetic medium comprises a plasticized fullerene derivative [6,6]-phenyl-$C_{61}$-butyric acid methyl ester (PCBM).

3. An apparatus for transferring energy to a microwave circuit or charged particle beam comprising:
   an active microwave chamber that is energized by an optical source and utilizes an active paramagnetic medium to transfer energy from the active medium to the microwave circuit or charged particle beam, wherein said paramagnetic medium is formed by the process comprising the steps:
   a. solvating fullerene derivative [6,6]-phenyl-$C_{61}$-butyric acid methyl ester (PCBM);
   b. dissolving polystyrene in the solvent-PCBM solution until a thick slurry is formed;
   c. pouring the solvent-polystyrene-PCBM solution into a mold of desired shape; and
   d. evaporating the solvent under vacuum to produce an optically transparent plastic loaded with the active PCBM compound.

4. An apparatus for transferring energy to a microwave circuit or charged particle beam comprising:
   an active microwave chamber that is energized by an optical source and utilizes an active paramagnetic medium to transfer energy from the active medium to the microwave circuit or charged particle beam, wherein sid paramagnetic medium is solvated by toluene.

5. A charged particle beam accelerator comprising:
   an elliptical mirror support structure;
   a light concentrator formed of a cylindrical tube located at a first foci of said elliptical mirror and forming an accelerating structure and containing a material selected from the group comprising:
      a liquid active paramagnetic microwave medium; and
      a plasticized solid microwave active medium; and
   a constant magnetic field within said elliptical mirror light concentrator and support structure.

6. The charged particle beam accelerator of claim 5, wherein frequency of microwaves and the applied magnetic field strength is controlled through the excitation of said medium by a visible light pulse located at a second focus of said elliptical mirror.

7. The charged particle beam accelerator of claim 6, wherein said visible light pulse is generated from a xenon flashlamp, laser or other optical source such that the effect of the optical excitation is to create a population inversion between two Zeeman levels in said active medium such that the excited said medium can then transfer its energy to a pulsed charged particle beam passing through said cylindrical tube.

8. The charged particle beam accelerator of claim 7, wherein said accelerating structure is either a resonant or nonresonant configuration.

9. The charged particle beam accelerator of claim 8, wherein said cylindrical tube comprises a paramagnetic medium of fullerene derivative [6,6]-phenyl-$C_{61}$-butyric acid methyl ester (PCBM).

10. The charged particle beam accelerator of claim 9, wherein said cylindrical tube comprises a paramagnetic medium of a plasticized fullerene derivative [6,6]-phenyl-$C_{61}$-butyric acid methyl ester (PCBM).

11. The charged particle beam accelerator of claim 10, wherein said paramagnetic medium is formed by the process comprising the steps:
   a. solvating fullerene derivative [6,6]-phenyl-$C_{61}$-butyric acid methyl ester (PCBM);
   b. dissolving polystyrene in the solvent-PCBM solution until a thick slurry is formed; and
   c. pouring the solvent-polystyrene-PCBM solution into a mold of desired shape;
   d. evaporating the solvent-PCBM solution under vacuum to produce an optically transparent plastic loaded with the active PCBM compound.

12. The charged particle beam accelerator of claim 11, wherein said solvent is toluene.

13. In an electronic filter forming a multi-pole active analog filter network, wherein the improvement comprises the use of an inductor within an analog circuit having active paramagnetic cores containing paramagnetic medium comprising fullerene derivative [6,6]-phenyl-$C_{61}$-butyric acid methyl ester (PCBM).

14. An active metamaterial incorporating paramagnetic materials comprising fullerene derivative [6,6]-phenyl-$C_{61}$-butyric acid methyl ester (PCBM), wherein the control of refractive properties of radiation passing through the electronic filter is accomplished using optical and magnetic means.

15. A highly sensitive magnetic field sensor having active paramagnetic circuits comprising paramagnetic material including fullerene derivative [6,6]-phenyl-$C_{61}$-butyric acid methyl ester (PCBM).

16. An active microwave resonator that is energized by an optical source and utilizes an active paramagnetic medium to transfer energy from the active medium to a microwave circuit or charged particle beam, wherein said paramagnetic medium comprises fullerene derivative [6,6]-phenyl-$C_{61}$-butyric acid methyl ester (PCBM).

17. The active microwave resonator of claim 16, wherein said paramagnetic medium comprises a plasticized fullerene derivative [6,6]-phenyl-$C_{61}$-butyric acid methyl ester (PCBM).

18. The active microwave resonator of claim 16, wherein said paramagnetic medium is formed by the process comprising the steps:
   a. solvating fullerene derivative [6,6]-phenyl-$C_{61}$-butyric acid methyl ester (PCBM);
   b. dissolving polystyrene in the solvent-PCBM solution until a thick slurry is formed;
   c. pouring the solvent-polystyrene-PCBM solution into a mold of desired shape; and
   d. evaporating the solvent-polystyrene-PCBM solution under vacuum to produce an optically transparent plastic loaded with the active PCBM compound.

19. The active microwave resonator of claim 18, wherein said solvent is toluene.

20. The active microwave resonator of claim 16, wherein said resonator is included in a compact linear particle accelerator, and wherein said compact linear particle accelerator is energized by an optical source and utilizes said active paramagnetic medium to transfer this energy to a charged particle beam.

21. The active microwave resonator of claim 16, wherein said resonator is included in a microwave amplifier or attenuator, and wherein said active paramagnetic medium's properties are adjustable using an external magnetic field.

22. In a multi-pole active analog filter network, wherein the improvement comprises an inductor having active paramagnetic cores of the paramagnetic material of claim 16.

23. An active metamaterial incorporating paramagnetic materials of claim 16, wherein control of refractive properties of said active paramagnetic medium is accomplished using optical and magnetic means.

24. A highly sensitive magnetic field sensor having active paramagnetic circuits comprising paramagnetic material of claim 16.

\* \* \* \* \*